United States Patent [19]
Nichtl et al.

[11] Patent Number: 5,972,720
[45] Date of Patent: Oct. 26, 1999

[54] STABILIZATION OF METAL CONJUGATES

[75] Inventors: Alfons Nichtl, Hohenpeissenberg; Peter Sluka, Weilheim, both of Germany

[73] Assignee: Roche Diagnostics GmbH, Mannheim, Germany

[21] Appl. No.: 08/869,738

[22] Filed: Jun. 5, 1997

[30] Foreign Application Priority Data

Jun. 5, 1996 [DE] Germany .............. 196 22 628

[51] Int. Cl.⁶ .................................. G01N 33/553
[52] U.S. Cl. ................ 436/525; 436/518; 435/7.21; 435/40.52
[58] Field of Search ............... 436/525, 518; 435/7.21, 40.52

[56] References Cited

U.S. PATENT DOCUMENTS

| | | | |
|---|---|---|---|
| 5,294,369 | 3/1994 | Shigekawa et al. | 252/313.1 |
| 5,376,556 | 12/1994 | Tarcha et al. | 435/525 |

FOREIGN PATENT DOCUMENTS

| | | |
|---|---|---|
| 0 441 120 A2 | 8/1991 | European Pat. Off. . |
| 0 489 465 A2 | 6/1992 | European Pat. Off. . |
| WO90/05303 | 5/1990 | WIPO . |
| WO93/21528 | 10/1993 | WIPO . |
| WO94/21240 | 9/1994 | WIPO . |

OTHER PUBLICATIONS

Grosdemange et al. XP–002063516 "Formation of Self–Assembled Monolayers by Chemisorption of Derivatives of Oligo (ethylene glycol) of Structure $HS(CH_2)_{11}(OCH_2CH_2)_mOH$ on Gold"; American Chemical Society 113, Nr.1 1991; pp. 13–20.

Prime et al. XP–002063517 "Self–Assembled Organic Monolayers: Model Systems for Studying Adsorption of Proteins at Surfaces"; Science (May 1991) pp. 1164–1167.

*Primary Examiner*—Donna C. Wortman
*Attorney, Agent, or Firm*—Nikaido, Marmelstein, Murray & Oram LLP

[57] ABSTRACT

The invention concerns a composition comprising colloidal particles to the surface of which biomolecules are adsorbed, wherein the composition additionally contains a polyethylene glycol substituted by thiol or/and disulfide groups. This composition can be used as a detection reagent in immunological test methods.

20 Claims, 1 Drawing Sheet

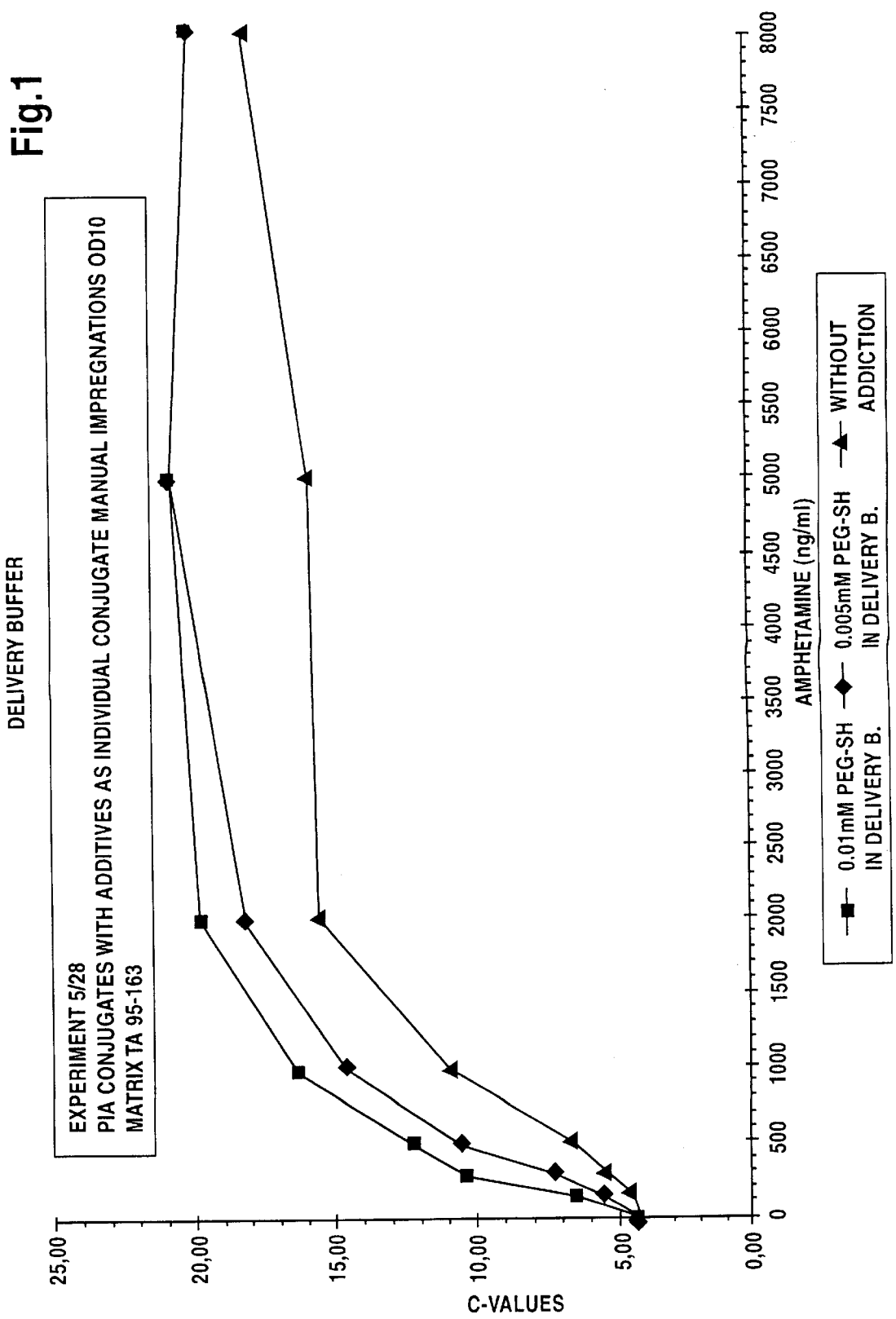

STABILIZATION OF METAL CONJUGATES

DESCRIPTION

The present invention concerns compositions which comprise a suspension of colloidal particles in an aqueous solution in which biomolecules are adsorbed to the surface of the particles.

Conjugates which are composed of biomolecules such as proteins or nucleic acids and colloidal particles are widely used in diagnostic and therapeutic procedures e.g. as markers in detection methods such as immunoassays or as microprojectiles for gene transfer. Particles composed of metals and metal compounds such as metal oxides, metal hydroxides, metal salts and polymer cores which are coated with metals or metal compounds can be used as particles (cf. e.g. U.S. Pat No. 4,313,734; Leuvering et al., J. Immunoassay 1 (1980), 77-91; Leuvering Dissertation (1984), Sol Particle Immunoassay (SPIA): The Use of Antibody Coated Particles as Labelled Antibodies in Various Types of Immunoassay; Uda et al., Anal. Biochem. 218 (1994), 259–264, DE-OS 41 32 133, page 3, lines 16–18, for applications as markers and Tang et al., Nature 356 (1992), 152–154; Eisenbraun et al., DNA and Cell Biology 12 (1993), 791–797; Williams et al., Proc. Natl. Acad. Sci. USA 88 (1991), 2726–2730 for applications for gene transfer). Furthermore it is also known that non-metallic colloidal particles such as carbon particles (van Amerongen, Anabiotic '92 (1993), 193–199) can also be used. At present colloidal gold particles are used most frequently.

In order to produce biomolecule-gold conjugates gold sols are firstly produced according to generally known processes by reducing tetrachloroauric acid. Subsequently the gold sols are loaded with the desired respective biomolecule e.g. proteins such as antibodies, protein A, protein G, streptavidin etc. The respective loading conditions (pH, buffer, concentration of biomolecules etc.) depend on the isoelectric point of the biomolecule, the MPA (minimal protecting amount) or/and the specific application of the conjugate (cf. e.g. De Mey, The Preparation and Use of Gold Probes, in: Immunocytochemistry, eds: J. M. Polak and S. V. Noorden, pp 115–145, Wright, Bristol 1986 and J. E. Beesley, Colloidal Gold: A New Perspective for Cytochemical Marking, Microscopy Handbooks 17, Oxford University Press, 1989, in particular pp 1–14). Explicit reference is made to the disclosure of these documents.

After the colloidal particles have been loaded with the respective desired biomolecule it is necessary to stabilize the conjugates. This stabilization is intended to minimize an aggregation of the particles and to saturate remaining free surfaces accessible to adsorption. In the state of the art inert proteins, e.g. bovine serum albumin, blood substitute mixtures etc., detergents such as TWEEN® 20, water-soluble technical polymers such as polyethylene glycol (molecular weight 20,000 D), polyvinylpyrrolidone, polyvinyl alcohol, polyvinyl sulfate, dextran and gelatin are used as stabilizers (cf. e.g. De Mey, Supra; Beesley, Supra; Behnke, Eur. J. Cell Biol. 41 (1986), 326–338; DE 24 20 531 C3; and Meisel et al., J. Phys. Chem. 85 (1981), 179–187). In addition the possibility of stabilizing gold sols by phospane complex ligands has also been described (Schmid et al., Z. Naturforsch. 45b (1994), 989–994).

The stabilizers used according to the state of the art bind adsorptively to the free surfaces of the metal particles. The stabilizers can be desorbed or displaced from the surfaces to a greater or lesser extent as a result of long storage or changes in the environmental conditions such as those which for example can occur in a test by contact with the sample (blood, serum, plasma, urine), incorporation of the conjugates in test strip fleeces etc. This leads to a deterioration of the aggregation stability and to an increase in the unspecific reactivity. Moreover a large number of the stabilizers used are poorly defined products some of which have variable quality e.g. bovine serum albumin, gelatin. As a result variations in the stabilizing effect may also occur.

Adsorption processes on particle surfaces are very complex and up to now are only partially understood. It is assumed that the adsorption occurs as a result of a combination of electrostatic interactions, Van-der-Waals forces and hydrophobic interactions (Beesely, Supra). In this process one or other type of binding can predominate depending on the type of the adsorbed biomolecule.

A publication by Prime and Whitesides (Science 252 (1991), 1154–1167) discloses that mixtures of hydrophobic (methyl-terminated) and hydrophobilic (hydroxyl-terminated, maltose-terminated and hexaethylene glycol-terminated) alkanethiols can suppress the adsorption of proteins to planar gold surfaces. A stabilization of the protein adsorption by alkanethiols is neither disclosed nor suggested.

Surprisingly it has now been found that polyethylene glycols substituted by thiol or/and disulfide groups are excellently suitable for the stabilization of biomolecule-particle conjugates. As a result of the stronger binding of the substituted polyethylene glycols to the particle surface compared to the stabilizers of the state of the art a substantial improvement is achieved with regard to the stability of the conjugates. This leads to an improved long-term stability and a lower aggregation tendency in solution, to a better stability towards changes in the environmental conditions and an improved test function e.g. chromatographic properties. It was particularly surprising that these improvements could be achieved without adversely affecting the function of the conjugates in the test such as by displacing the biomolecules by the substituted polyethylene glycol or by possible interactions of the biomolecules with the substituted polyethylene glycol (e.g. interactions between SH groups of the biomolecules and SH groups of the substituted polyethylene glycol). In contrast one even finds an improved test performance in many test formats when the substituted polyethylene glycols are used which can be exhibited as a reduction of the lower detection limit or/and a higher dynamic range (steeper detection curve). Stabilizers that are suitable for this are short-chained defined substituted polyethylene glycols with for example at least two ethylene oxide units, high molecular substituted polyethylene glycols with a statistical molar mass distribution and mixtures thereof.

One subject matter of the present invention is thus a composition comprising colloidal particles on whose surface biomolecules are adsorbed, the composition additionally containing a polyethylene glycol substituted by thiol or/and disulfide groups which is preferably co-adsorbed to the surface of the particles.

The composition according to the invention can be present as an aqueous suspension or also immobilized for example on a chromatographic material such as an absorbent paper. If the composition is in the form of an aqueous suspension it preferably additionally contains the substituted polyethylene glycol in the buffer in a dissolved form as well as co-adsorbed on the surface of the particles.

The particles can be metallic or non-metallic particles such as carbon particles. Metallic particles such as particles of metals, metal oxides, metal hydroxides, metal compounds or particles coated with metals or metal compounds are preferred. Metal particles are particularly preferred.

The metal particles are preferably noble metal particles e.g. metals selected from the group comprising gold, silver, copper, platinum, palladium and mixtures thereof. Gold particles are particularly preferred.

The average diameter of the particles is in the range of 1–1000 nm which is usual in the state of the art and can be varied according to the application purpose. The average diameter of the particles is preferably in the range of 2–200 nm and particularly preferably 2–100 nm.

The biomolecules adsorbed to the surface of the particles are preferably selected from the group comprising proteins, glycoproteins, peptides, nucleic acids, peptidic nucleic acids, saccharides, antigens and haptens. Biomolecules are particularly preferably selected from the group comprising antibodies, antibody fragments, lectins, enzymes, streptavidin, avidin, protein A, antigens such as recombinant polypeptides or multiple antigens (cf. WO96/03652), e.g. polyhaptens (several haptens or peptides coupled to a carrier such as dextran or to a protein), peptides and haptens (low molecular substances preferably with a MW≦1500 such as biotin, fluorescein or digoxigenin). Reference is made to the aforementioned review article by De Mey and Beesley with regard to the exact conditions for adsorbing these biomolecules to gold particles.

A thiol-substituted polyethylene glycol that is suitable as a stabilizer is preferably an essentially linear chain-like molecule which carries a thiol group at at least one end of the chain. Preferably there is a thiol group at one end and a group that is different from thiol or disulfide at the other end. A disulfide-substituted polyethylene glycol that is suitable as a stabilizer is preferably also an essentially linear chain-like molecule which contains at least one SS bridge within the chain. The molecule preferably contains only one SS bridge and groups that are different from thiol or disulfide at its ends. Mixtures of disulfide-substituted and thiol-substituted compounds are also suitable as a stabilizer.

Hence the polyethylene glycol substituted by thiol groups or/and disulfide groups preferably has the following general structural formula:

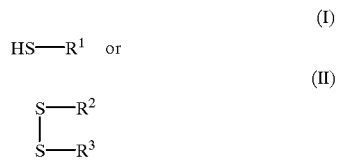

in which the residue $R^1$ as well as at least one of the residues $R^2$ and $R^3$ is an organic residue which contains at least 2 and preferably at least 3 ($CH_2$—$CH_2$—O) groups.

The residues $R_1$, $R_2$ and $R_3$ of the substituted polyethylene glycols which contain the ethylene oxide units are preferably selected such that the compounds have a maximum average molecular weight of about 50,000 D and particularly preferably a maximum average molecular weight of about 25,000 D. The terminal groups of the residues $R_1$, $R_2$ and $R_3$ can be any desired groups but preferably OH groups or/and O-alkyl groups such as O—$C_1$-$C_4$ alkyl groups such as O-methyl or O-ethyl groups.

A preferred example of a suitable substituted polyethylene glycol is a methoxy-polyethylene-glycol-SH with an average molecular weight of ca. 5,000 D which is commercially available from Shearwater Polymers Inc. On the other hand it is also possible to use short defined thiol-substituted or disulfide-substituted polyethylene glycols which for example contain 2–10 ethylene oxide units.

The compositions according to the invention can be used as a detection reagent in particular as an immunological detection reagent. In a first preferred embodiment the detection reagent is used in an immunoassay i.e. in a method for the determination of an analyte in a sample liquid by means of immunological methods e.g. by a competitive assay in which a labelled analyte analogue or a labelled analyte-specific receptor e.g. an antibody is used, or a sandwich assay in which a labelled analyte-specific receptor or a labelled further receptor capable of binding to the analyte-specific receptor is used. Preferred examples are pregnancy tests e.g. tests for the detection of human chorionic gonadotropin (HCG), or methods for the detection of drugs such as cocaine or amphetamines, human serum albumin, troponin T, myoglobin and immunoglobulins such as anti-HIV antibodies. Particularly preferred application forms are rapid tests in which the sample to be determined is applied to an absorptive material containing the detection reagent e.g. a test strip. A second particularly preferred embodiment in which the stabilized composition according to the invention can be used is the staining of tissue sections.

In addition the compositions according to the invention can of course also be used for all other applications which are known for biomolecule-particle conjugates e.g. for gene transfer.

Yet a further subject matter of the present invention is a process for the stabilization of conjugates composed of colloidal particles and biomolecules in which a polyethylene glycol substituted by thiol groups or/and disulfide groups is added to the conjugate. In this manner it is possible to achieve an increased long-term stability of the conjugates (>1.5 years) as well as an improved pH stability and an improved stability towards the presence of other substances.

The substituted polyethylene glycol is preferably added in an amount which yields a final concentration of 0.1 μM to 1 μM in particular of 1 μM to 100 μM.

Furthermore additional stabilizers known from the state of the art such as inert proteins e.g. bovine serum albumin or/and unsubstituted polyethylene glycols can be added.

Finally the present invention also concerns a test kit for an immunological method of detection which contains a stabilized composition according to the invention as the detection reagent.

It is intended to further elucidate the invention by the figures and the following examples.

FIG. 1 shows a comparison of the test performance of antibody-gold conjugates stabilized according to the invention with that of conjugates of the state of the art.

EXAMPLE 1

Synthesis of Thiol-Substituted Polyethylene Glycol Compounds 25 g tetraethylene glycol monomethyl ether (Kodak Co.) was reacted with 25 g tosyl chloride in 150 ml pyridine. The reaction mixture was diluted with water and subsequently with ethyl acetate. The tosylate (13 g) obtained by concentration was reacted at 150° C. with 15 g phthalimide potassium salt in DMF. The reaction mixture was diluted with water and extracted with ethyl acetate. The product (10.2 g) obtained after rotary evaporation was taken up in 50 ml methanol, filtered and admixed with 1.83 ml hydrazine hydrate. The mixture was boiled under reflux for 2 hours, cooled, admixed with concentrated HCl and the precipitate that settled out was removed by filtration.

The filtrate was alkalinized with 3 N NaOH and subsequently extracted with chloroform. After rotary evaporation 3.11 g of a viscous oil was obtained.

500 mg of this oil was dissolved with 244 mg triethylamine in 10 ml THF. 591 mg S-acetylthiopropionic acid-O-succinimide ester in 20 ml THF was added dropwise to this solution. This solution was stirred for 24 hours at room temperature, rotary evaporated and purified over a silica gel column.

In order to cleave the acetyl group to release the thiol groups, 15 ml 25% ammonia solution was added to a solution of 550 mg of the product in water. The preparation was purified by column chromatography. 300 mg of a monomethoxy tetraethylene glycol propionamido-SH compound was obtained.

EXAMPLE 2
Production of Protein-Gold Conjugates

A solution of the protein adsorbed to gold particles was dialysed against a suitable loading buffer or diluted with the loading buffer. Subsequently aggregates that may have formed were removed by centrifugation or filtration through a 0.2 $\mu$m filter.

The pH value of the solution containing the colloidal gold particles was adjusted with $K_2CO_3$ to the pH value of the protein solution. Then the colloidal gold solution was added to the protein while stirring.

The protein-gold conjugates prepared in this manner were stabilized according to the state of the art by adding a BSA solution up to a final concentration of 0.1% –1% (w/v) or by adding a polyethylene glycol solution up to a final concentration of 0.01% –0.1% (w/v).

Subsequently the protein-gold conjugates were purified and concentrated and the desired storage buffer conditions were set e.g. 20 mM Tris, 100 mM NaCl pH 8, 1% BSA or/and 0.01% –0.1% PEG, $NaN_3$.

EXAMPLE 3
Pre-Saturation of the Gold Sol by PEG-SH in Comparison to PEG

When the gold sol was pre-saturated according to example 2 by adding $10^{-5}$ M PEG-SH (commercial PEG-SH MW 5000 from Shearwater Polymers, Inc. or PEG-SH according to example 1) or PEG before adding a monoclonal anti-human serum albumin mouse IgG antibody to 20 nm gold particles, it was found that PEG can be displaced by the antibody from the gold sol but not PEG-SH.

EXAMPLE 4
Application of protein-gold conjugates stabilized according to the invention in tests for the detection of human serum albumin and HCG Conjugates of monoclonal anti-human serum albumin and anti-HCG antibodies on gold particles were prepared according to the procedure described in example 2. After the conjugates were formed they were stabilized by adding PEG-SH at a final concentration of $10^{-6}$ M to $10^{-4}$ M.

The addition of PEG-SH as the sole stabilizer directly after the antibody loading, the addition of PEG-SH and BSA (successively or in a mixture) as a stabilizer directly after antibody addition and the addition of PEG-SH as a stabilizer to the storage buffer (final concentration $10^{-4}$ M to $10^{-5}$ M) were tested.

The tests were carried out on a test strip as competitive one-step tests.

It was found that the function of conjugates composed of monoclonal anti-HSA antibodies and gold particles was not adversely affected by the stabilization with PEG-SH.

EXAMPLE 5
Stability of Gold-Conjugates Stabilized by PEG-SH

A determination of the antibody-gold conjugates prepared in example 4 after a storage period of 1.5 years showed that no antibodies bled and that the function was still completely present.

EXAMPLE 6
pH Stability of Antibody-Gold Conjugates

Monoclonal anti-HCG mouse IgG antibodies were adsorbed to 40 nm gold particles according to the procedure described in example 2. Subsequently a resaturation was carried out as described in the legend of tables 1a, 1b and 1c.

The stability of these conjugates was tested in an impregnation buffer (50 mM HEPES pH 7.0, 100 mM NaCl, 2.0% sucrose, 0.1% BSA, 0.2% Brij 35) which had been adjusted with HCl or NaOH to various pH values.

Test procedure: The actual OD at 520 nm was measured on all tested gold conjugates. Then each batch was diluted with 5 impregnation buffers of various pH values to an OD of ca. 8 and checked immediately and after 1 and 6 hours on a photometer.

Table 1a shows the results for an antibody-gold conjugate according to the invention which was stabilized by PEG 20,000 added to a final concentration of 0.05% and subsequently PEG-SH to a final concentration of 1 $\mu$M.

Table 1b shows the results for a further antibody-gold conjugate according to the invention which was stabilized by PEG-SH added to a final concentration of 1 $\mu$M.

Table 1c shows the results for an antibody-gold conjugate of the state of the art which was stabilized by saturation to a final concentration of 0.05% PEG.

TABLE 1a

| PH value of the conjugate stock solution | pH value of the impregnation buffer | pH value after dilution to OD8 | OD of the conjugate stock solution | OD immediately after dilution | OD after 1 h | OD after 6 h |
|---|---|---|---|---|---|---|
| 8.5 | 4.3 | 6.7 | 19.97 | 8.3 | 8.2 | 8.4 |
|  | 5.3 | 7.1 |  | 8.3 | 8.2 | 8.4 |
|  | 7.0 | 7.6 |  | 8.3 | 8.3 | 8.5 |
|  | 7.5 | 8.2 |  | 8.2 | 8.3 | 8.4 |
|  | 8.2 | 8.9 |  | 8.3 | 8.3 | 8.4 |

TABLE 1b

| PH value of the conjugate stock solution | pH value of the impregnation buffer | pH value after dilution to OD8 | OD of the conjugate stock solution | OD immediately after dilution | OD after 1 h | OD after 6 h |
|---|---|---|---|---|---|---|
| 8.5 | 4.3 | 6.7 | 21.49 | 8.4 | 8.4 | 8.5 |
|  | 5.3 | 7.1 |  | 8.5 | 8.5 | 8.6 |
|  | 7.0 | 7.6 |  | 8.4 | 8.4 | 8.5 |
|  | 7.5 | 8.2 |  | 8.5 | 8.6 | 8.6 |
|  | 8.2 | 8.9 |  | 8.3 | 8.2 | 8.5 |

TABLE 1c

| PH value of the conjugate stock solution | pH value of the impregnation buffer | pH value after dilution to OD8 | OD of the conjugate stock solution | OD immediately after dilution | OD after 1 h | OD after 6 h |
|---|---|---|---|---|---|---|
| 8.6 | 4.5 | 6.6 | 20.20 | 8.1 | 6.4 | 5.2 |
|  | 4.8 | 7.4 |  | 7.8 | 6.4 | 6.2 |
|  | 5.2 | 7.5 |  | 7.9 | 7.3 | 7.3 |
|  | 6.0 | 7.8 |  | 8.1 | 8.0 | 8.1 |
|  | 7.5 | 8.0 |  | 7.9 | 8.0 | 8.1 |
|  | 8.8 | 8.6 |  | 8.0 | 8.0 | 8.2 |

These results show that in the case of the gold conjugate of the state of the art a considerable instability (decrease of the OD) can already be observed after one hour at pH values in the acidic and neutral range. In contrast the OD of the conjugates according to the invention remains constant. This shows that the conjugates according to the invention have a considerably improved pH stability compared to the conjugates of the state of the art.

EXAMPLE 7

Comparison of the test function of antibody-gold conjugates according to the invention with conjugates of the state of the art.

A conjugate composed of a polyclonal anti-amphetamine sheep IgG antibody and 20 nm gold particles was prepared. The resaturation was carried out by adding 0.1% BSA. The storage buffer contained 2% BSA.

$5 \times 10^{-6}$ M or $10^{-5}$ M PEG-SH was added after the resaturation or to the storage buffer in order to stabilize the conjugates according to the invention.

The amphetamine detection was carried out on a test strip as a competitive one-step test.

The result of this experiment is shown in FIG. 1. It can be seen that the gold conjugate without addition of PEG-SH has a considerably flatter test curve and hence a poorer test function than the conjugates stabilized according to the invention by PEG-SH. An addition of $10^{-5}$ M PEG-SH leads to an even greater improvement than the addition of $5 \times 10^{-6}$ M PEG-SH.

We claim:

1. Colloidal particles to the surface of which are co-adsorbed: 1) biomolecules and 2) polyethylene qlycol substituted by thiol and/or disulfide groups.

2. The colloidal particles as claimed in claim 1, wherein the particles are noble metal particles.

3. The colloidal particles as claimed in claim 2, wherein the noble metals are selected from the group consisting of Au, Ag, Cu, Pt, Pd and mixtures thereof.

4. The colloidal particles as claimed in claim 3, wherein the noble metal is Au.

5. The colloidal particles as claimed in claim 1, wherein the average diameter of the particles is in the range of 1 nm to 1000 nm.

6. The colloidal particles as claimed in claim 1, wherein the biomolecules are selected from the group consisting of proteins, glycoproteins, peptides, nucleic acids, peptidic nucleic acids, saccharides, antigens and haptens.

7. The colloidal particles as claimed in claim 6, wherein the biomolecules are selected from the group consisting of antibodies, antibody fragments, lectins, enzymes, streptavidin, avidin, protein A, recombinant polypeptides, peptides, haptens and polyhaptens.

8. The colloidal particles as claimed in claim 1, wherein the substituted polyethylene glycol has the general structural formula.

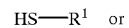 (I)

 (II)

in which the residue $R^1$ and the residues $R^2$ and $R^3$ are organic residues which contain at least 2 ($CH_2$—$CH_2$—O) groups.

9. The colloidal particles as claimed in claim 8, wherein the residues $R^1$, $R^2$ and $R^3$ have OH groups or/and O-alkyl groups as the terminal groups.

10. The colloidal particles as claimed in claim 1, wherein the substituted polyethylene glycol has a maximum average molecular weight of about 50,000 D.

11. A method for the detection of an analyte in a sample, comprising contacting said sample with the colloidal particles as claimed in claim 1 and detecting binding of the analyte to the colloidal particles.

12. A method as claimed in claim 11 wherein said detection is conducted by an immunoassay analysis.

13. A method as claimed in claim 11 wherein said colloidal particles are present on a chromatographic material.

14. A method as claimed in claim 11 comprising staining tissue sections.

15. A composition consisting essentially of colloidal particles with co-adsorbed substituted polyethylene glycol and biomolecules .

16. A test kit for an immunological method of detection, wherein it contains a composition as claimed in claim 15 as the detection reagent.

17. A process for making colloidal particles with co-adsorbed biomolecules and polyethylene glycol substituted by thiol or/and disulfide groups, said process comprising adding to said colloidal particles and biomolecules a polyethylene glycol substituted with thiol or/and disulfide groups.

18. The process as claimed in claim 17, wherein the polyethylene glycol is added in an amount which yields a final concentration of 0.1 $\mu$M to 1 mM.

19. The process as claimed in claim 17, wherein a further stabilizer is additionally added.

20. The process as claimed in claim 19, wherein said further stabilizer comprises an inert protein or/and polyethylene glycol.

* * * * *